United States Patent [19]

Tanaka et al.

[11] Patent Number: 4,500,865
[45] Date of Patent: Feb. 19, 1985

[54] FLUID LEAKAGE DETECTING ELEMENT

[75] Inventors: Yoshito Tanaka; Ken Ichiryu, both of Ibaraki; Naohiko Iwata, Hitachi, all of Japan

[73] Assignee: Hitachi, Ltd., Tokyo, Japan

[21] Appl. No.: 459,211

[22] Filed: Jan. 19, 1983

[30] Foreign Application Priority Data

Feb. 26, 1982 [JP] Japan ................. 57-29018

[51] Int. Cl.³ .............. H01C 7/00; H01C 1/012; G01N 25/72
[52] U.S. Cl. ........................... 338/13; 338/7; 338/9; 338/292; 338/307; 374/4; 374/5
[58] Field of Search .............. 338/13, 283, 3, 7, 9, 338/22 R, 277, 280, 292, 306–309; 374/4, 5; 340/605; 324/65 R, 52

[56] References Cited

U.S. PATENT DOCUMENTS

| 3,266,661 | 8/1966 | Dates ................. 338/283 X |
| 3,665,756 | 5/1972 | Russell ................. 338/3 X |
| 4,286,377 | 9/1981 | Hurko et al. ............. 338/25 X |

FOREIGN PATENT DOCUMENTS

| 55-113928 | 9/1980 | Japan . |
| 55-151250 | 11/1980 | Japan . |
| 56-57930 | 5/1981 | Japan ................. 324/65 R |
| DE81/114 | 2/1982 | PCT Int'l. Appl. ............ 340/605 |

OTHER PUBLICATIONS

Arcus et al., "Leak Detectors for Chemical Distribution System", *IBM Tech. Disc.*, vol. 18, No. 10, pp. 3271–3272, Mar. 1976.
Wyatt, R. F., "The Design of Thick Film Resistors", *Progress in Miniaturization*, May 1970.

*Primary Examiner*—Roy N. Envall, Jr.
*Assistant Examiner*—C. N. Sears
*Attorney, Agent, or Firm*—Antonelli, Terry & Wands

[57] ABSTRACT

A fluid leakage detecting element comprises a heat generating resistive member and a temperature compensating resistive member disposed on a substrate. Each of the resistive members is prepared in the form of a paste of a metal which has a high temperature coefficient and a high thermal conductivity and whose melting point is higher than the baking temperature of the substrate. These resistive members are printed in thick film form on the substrate which is sufficiently electrical insulating and has a high thermal conductivity.

8 Claims, 3 Drawing Figures

FLUID LEAKAGE DETECTING ELEMENT

BACKGROUND OF THE INVENTION

This invention relates to a detecting element utilized in an improved electrical resistance type of fluid leakage detecting apparatus for detecting external leakage of fluid from piping systems and equipments installed therein. More particularly, this invention relates to a fluid leakage detecting element for use in a fluid leakage detecting apparatus suitable for detecting a variety of modes of fluid leakage ranging from leakage in a very slight quantity such as oozing-out to leakage in a large quantity from plant equipments, pressure vessels, oil pipe lines, oil tanks, and pumps, motors and various control valves controlled by various kinds of fluids.

Generally, in a plant such as an oil plant, many fluid piping systems are closely arranged for operating the plant, and many valves and other fittings are installed in the piping systems.

Cracks tend to occur on the pipes of the piping systems and valves and other fittings installed therein on gaps tend to appear at the connections, as a result of an extended period of time of use or impartation of an external force by, for example, an earthquake. Occurrence of a crack on any one of the pipes, valves and other fittings of the piping systems or appearance of a gap at any one of the connections will result in leakage of fluid through the crack or gap, and this fluid leakage will lead to impairment of the safety of the plant. Therefore, an apparatus for detecting leakage of fluid is used to ensure the safety of the plant.

In one type of prior art fluid leakage detecting apparatus, a change in the electrical resistance value of a resistive element due to its contact with a fluid to be detected is utilized for the detection of fluid leakage, as, for example, disclosed in Japanese patent application Laid-open No. 113928/80 and Japanese patent application Laid-open No. 151250/80.

In such a resistance type fluid leakage detecting apparatus, the detection sensitivity, response characteristic, anticorrosion property, mechanical strength and reliability of the resistive element must be fully taken into consideration. However, none of the prior art detecting apparatus have been fully satisfactory in these aspects.

SUMMARY OF THE INVENTION

It is an object of the present invention to provide an improved electrical resistance type of fluid leakage detecting element which has a high mechanical strength and is highly reliable.

Another object of the present invention is to provide a fluid leakage detecting element of the aforementioned type which can be easily manufactured.

In accordance with the present invention which attains the above objects, there is provided a fluid leakage detecting element comprising a heat generating resistive member and a temperature compensating resistive member disposed on a substrate, each of the heat generating resistive member and the temperature compensating resistive member being prepared in the form of a paste of a metal which has a high temperature coefficient and a high thermal conductivity and whose melting point is higher than the firing temperature of the substrate, the resistive members being printed in thick film form on the substrate which is sufficiently electrical insulating and has a high thermal conductivity.

Other objects, features and advantages of the present invention will be apparent from the following detailed description of preferred embodiments thereof taken in conjunction with the accompanying drawings.

DESCRIPTION OF THE PREFERRED EMBODIMENTS

Figure 1:
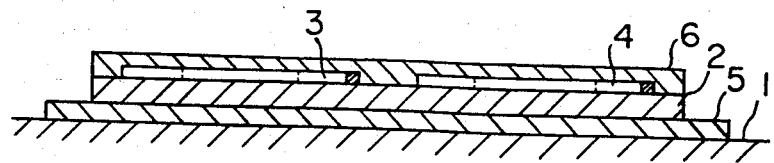
FIG. 1 is a longitudinal sectional view of an embodiment of the fluid leakage detecting element according to the present invention.
Figure 2:
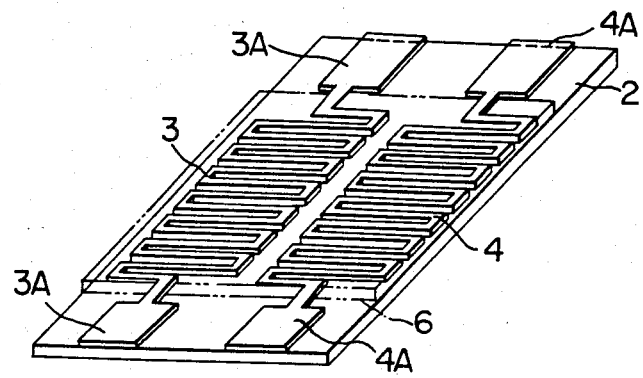
FIG. 2 is a perspective view of the element shown in FIG. 1.

FIGS. 1 and 2 show a preferred embodiment of the fluid leakage detecting element according to the present invention. Referring to FIGS. 1 and 2, the detecting element is mounted on a body 1 at its position where a fluid may leak out. The detecting element comprises a ceramic substrate 2, a heat generating resistive member 3, a temperature compensating resistive member 4, and a heat insulator 5. The ceramic substrate 2 is in the form of a thin sheet of a ceramic material which has a high thermal conductivity and is sufficiently heat resistive and electrical insulating. The thickness of the ceramic sheet 2 is about 0.3 mm to 0.5 mm. The heat generating resistive member 3 and the temperature compensating resistive member 4 are each in the form of a thick film of a metal such as tungsten which has a melting point higher than the firing temperature of the ceramic substrate 2. The heat insulator 5 is made of a synthetic resin which is sufficiently resistive to chemicals and heat and has a low thermal conductivity. This heat insulator 5 is bonded or otherwise fixed to the back surface of the ceramic substrate 2. Terminals 3A and 4A of the respective resistive members 3 and 4 are disposed on the both longitudinal ends of the ceramic substrate 2 as shown. The resistive members 3 and 4 are formed in a zigzag pattern so that they have large electrical resistance values.

The heat generating resistive member 3 and temperature compensating resistive member 4 are printed in thick film form on the ceramic substrate 2 by process which will be described now.

Figure 3:
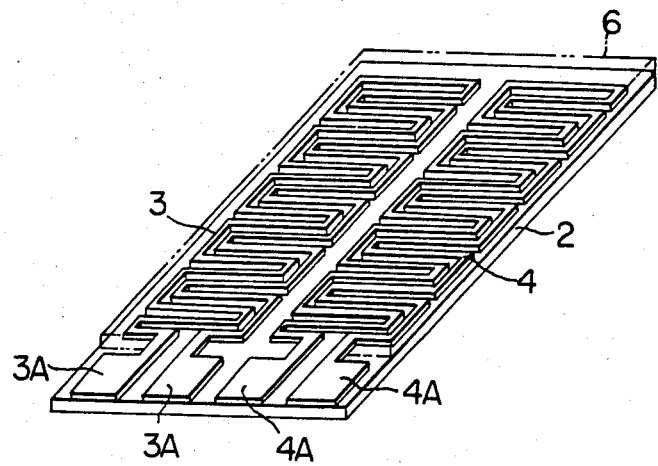
FIG. 3 is a perspective view of another embodiment of the fluid leakage detecting element according to the present invention.

Pastes of tungsten prepared for providing resistive properties adapted for the resistive members 3 and 4 are printed in thick film form on the substrate 2 of non-baked ceramic sheet, so as to provide required resistor patterns as shown in FIGS. 2 or 3. Then, in order to protect the printed resistive members 3 and 4, a paste of alumina is coated on the resistive members 3 and 4 to provide an insulating coating 6. Subsequently, the non-baked ceramic substrate 2 is baked at a temperature lower than the melting point of tungsten forming the resistive members 3 and 4. Since the melting point of tungsten is 3,410° C. which is far higher than the baking temperature, 1,600° C., of the ceramic substrate 2, there is utterly no possibility that tungsten vaporizes or becomes porous during baking of the ceramic substrate 2. As a result of this baking treatment, tungsten combines chemically, e.g. is bonded, with the ceramic material, and the thin insulating coating 6 of alumina coated on the surface of tungsten is also baked. Therefore, the resistive members 3 and 4 of tungsten are firmly sandwiched between the ceramic substrate 2 and the insulating coating 6 without separating from the ceramic substrate 2, and the mechanical strength which has been one of the drawbacks of the prior art element is greatly increased to greatly improve the reliability. When compared with platinum which shows a high anti-corrosiveness, tungsten is defective in that it has a chemical property relatively soluble to concentrated nitric acid and hydrofluoric acid. However, covering of the surface of the resistive members 3 and 4 with the insulating coating 6 of alumina in the element of the present invention eliminates such a problem. Further, because of the fact that the thermal conductivity and temperature coefficient of tungsten are higher than those of platinum, incorporation of the detecting element of the present invention in a fluid leakage detecting apparatus of the type electrically detecting a change in the thermal conductivity or resistance can greatly increase the sensitivity of detection of fluid leakage.

Although the ceramic substrate 2 may be directly disposed on the body 1, the heat insulator 5 is preferably interposed between the ceramic substrate 2 and the body 1. As described already, the material of this heat insulator 5 is preferably a synthetic resin which is sufficiently resistive to chemicals and heat and has a low thermal conductivity. Such a synthetic resin is, for example, a polyimide, a polyphenyl oxide or a polyamide. The polyimide resin is especially preferable in that it can withstand heating up to a high temperature of 525° C.

According to the present invention, the ceramic substrate 2 having the heat insulator 5 in the form of a thin film of a snythetic resin bonded to the back surface thereof is bonded or otherwise fixed to the body 1 which is the object of detection of fluid leakage, as described above, so that conduction of the temperature of the ceramic substrate 2 heated by the current flowing through the heat generating resistive member 3 as well as conduction of the temperature of the body 1 to the ceramic substrate 2 can be reliably prevented. By virtue of the above fact, the surface temperature of the ceramic substrate 2 can be maintained stable or substantially constant, and erosion of the ceramic substrate 2 can also be prevented. Thus, the detecting element of the invention is used by fixing the detecting element to the body 1 and passing current through the heat generating resistive member 3. Variations in the electrical resistance of the resistive member 3 are then detected in a conventional manner for the detection of fluid leakage since contact of a leaked fluid with the current carrying resistive member 3 will change the resistance thereof. The resistance of the temperature compensating resistive member 4 can also be detected in a conventional manner.

In the above embodiment, the terminals 3A and 4A of the respective resistive members 3 and 4 are disposed on the both longitudinal ends of the ceramic substrate 2. However, these terminals 3A and 4A may be disposed in a concentrated mode on only one of the longitudinal ends of the ceramic substrate 2 as shown in FIG. 3 which illustrates a modification of the first embodiment. Concentrated disposition of the terminals 3A and 4A as shown in FIG. 3 facilitates wiring connections to these terminals 3A and 4A.

Further, although the heat generating resistive member 3 and the temperature compensating resistive member 4 are disposed adjacent to each other on the ceramic substrate 2 in the aforementioned embodiments, they may be disposed on separate ceramic substrates respectively, or the heat generating resistive member 3 only may be used without providing the temperature compensating resistive member 4.

It will be understood from the foregoing detailed description that the present invention provides a highly reliable, fluid leakage detecting element in which resistive members are printed in thick film form on a ceramic substrate and firmly sandwiched between an insulating coating and the ceramic substrate to increase the mechanical strength of the element and to eliminate the possibility of separation of the resistive members from the ceramic substrate.

We claim:

1. A fluid leakage detecting element comprising a substrate of electrical insulating material having a high thermal conductivity and having two opposing surfaces, one of which is adopted to be attached to a portion of a subject where a fluid contained in said subject may leak, a heat generating resistive member, said member being provided in thick film form on the other surface of said substrate and made of tungsten which has a high temperature coefficient, a high thermal conductivity and a melting point higher than the baking temperature of said substrate, wherein an insulating coating of alumina is provided covering the surface of said resistive member and wherein said substrate is bonded to said tungsten resistive member, and a heat insulator of a material which is sufficiently resistive to chemicals and heat and has a low thermal conductivity is disposed on said attachable surface of said substrate.

2. A fluid leakage detecting element as claimed in claim 1, wherein the material of said heat insulator is a synthetic resin.

3. A fluid leakage detecting element as claimed in claim 1, wherein said substrate is formed of a thin sheet of ceramic material.

4. A fluid leakage detecting element as claimed in claim 3, wherein said sheet of ceramic material has a thickness of 0.3 mm to 0.5 mm.

5. A fluid leakage detecting element comprising a substrate of electrical insulating material having a high thermal conductivity and having two opposing surfaces, one of which is adopted to be attached to a portion of a subject where a fluid contained in said subject may leak, a heat generating resistive member and a temperature compensating resistive member, said members being provided in thick film form on the other surface of said substrate and made of tungsten which has a high temperature coefficient, a high thermal conductivity and a melting point higher than the baking temperature of said substrate, and an insulating coating of alumina covering the surface of said resistive members with said tungsten resistive members being bonded to said substrate, and a heat insulator of a material which is sufficiently resistive to chemicals and heat and has a low thermal conductivity is disposed on said attachable surface of said substrate.

6. A fluid leakage detecting element as claimed in claim 5, wherein said resistive members are disposed substantially in parallel along a longitudinal direction of said substrate and terminals of said resistive members are disposed on both longitudinal ends of said substrate.

7. A fluid leakage detecting element as claimed in claim 5, wherein said resistive members are disposed substantially in parallel along a longitudinal direction of said substrate and terminals of said resistive members are disposed only on one of the longitudinal ends of said substrate.

8. A fluid leakage detecting element as claimed in claim 4, wherein the material of said heat insulator is a synethetic resin.

* * * * *